(12) United States Patent
Thomsen et al.

(10) Patent No.: US 8,311,181 B2
(45) Date of Patent: Nov. 13, 2012

(54) APPARATUS AND METHOD OF VISUALIZING MULTI-ENERGY IMAGING DATA

(75) Inventors: Brian William Thomsen, Milwaukee, WI (US); Paulo Mendonca, Clifton Park, NY (US); Rahul Bhotika, Albany, NY (US)

(73) Assignee: General Electric Company, Schenectadt, NY (US)

( * ) Notice: Subject to any disclaimer, the term of this patent is extended or adjusted under 35 U.S.C. 154(b) by 0 days.

(21) Appl. No.: 12/697,419

(22) Filed: Feb. 1, 2010

(65) Prior Publication Data

US 2010/0135565 A1 Jun. 3, 2010

Related U.S. Application Data

(63) Continuation-in-part of application No. 12/315,184, filed on Nov. 28, 2008.

(60) Provisional application No. 61/264,286, filed on Nov. 25, 2009.

(51) Int. Cl.
*A61B 6/00* (2006.01)
*H05G 1/64* (2006.01)
*G06K 9/00* (2006.01)

(52) U.S. Cl. .............. 378/5; 378/98.9; 382/130

(58) Field of Classification Search .......... 378/4, 5, 378/98.9, 98.11, 98.12
See application file for complete search history.

(56) References Cited

U.S. PATENT DOCUMENTS

| | | | | |
|---|---|---|---|---|
| 3,848,130 A | * | 11/1974 | Macovski | 378/98.9 |
| 4,506,327 A | * | 3/1985 | Tam | 378/5 |
| 4,686,695 A | * | 8/1987 | Macovski | 378/146 |
| 5,115,394 A | * | 5/1992 | Walters | 382/131 |
| 5,155,365 A | * | 10/1992 | Cann et al. | 250/363.02 |
| 5,521,955 A | * | 5/1996 | Gohno et al. | 378/18 |
| 5,524,133 A | * | 6/1996 | Neale et al. | 378/53 |
| 7,724,865 B2 | * | 5/2010 | Wu et al. | 378/5 |
| 7,778,454 B2 | * | 8/2010 | Grasruck et al. | 382/128 |
| 2002/0181755 A1 | * | 12/2002 | Lee et al. | 382/132 |
| 2003/0147489 A1 | * | 8/2003 | Bijjani et al. | 378/4 |
| 2003/0194115 A1 | * | 10/2003 | Kaufhold et al. | 382/128 |

(Continued)

FOREIGN PATENT DOCUMENTS

| | | | | |
|---|---|---|---|---|
| GB | 2088050 | A | * | 6/1982 |
| JP | 0549858 | A | * | 7/1993 |
| WO | WO 2005076221 | A1 | * | 8/2005 |

OTHER PUBLICATIONS

Yu et al., Pre-reconstruction Three-material Decomposition in Dual-energy CT, Medical Imaging, Proc. of SPIE, vol. 7258, 2009, pp. 1-8.*

(Continued)

*Primary Examiner* — Alexander H Taningco
(74) *Attorney, Agent, or Firm* — Ziolkowski Patent Solutions Group, SC

(57) ABSTRACT

An imaging system includes an x-ray source configured to emit a beam of x-rays toward an object to be imaged, a detector configured to receive x-rays that are attenuated by the object, a data acquisition system (DAS) operably coupled to the detector, and a computer operably coupled to the DAS and programmed to obtain scan data with two or more incident energy spectra, decompose the obtained scan data into at least three basis materials, generate an image of one of the at least three basis materials using the decomposed scan data, and replace at least one pixel in the image using decomposed data of another of the at least three basis materials.

31 Claims, 10 Drawing Sheets

U.S. PATENT DOCUMENTS

| | | | |
|---|---|---|---|
| 2004/0101086 A1* | 5/2004 | Sabol et al. | 378/4 |
| 2004/0184574 A1* | 9/2004 | Wu et al. | 378/5 |
| 2005/0084063 A1* | 4/2005 | Heismann et al. | 378/53 |
| 2005/0084069 A1* | 4/2005 | Du et al. | 378/98.9 |
| 2005/0163283 A1* | 7/2005 | Bruder et al. | 378/98.11 |
| 2007/0217570 A1* | 9/2007 | Grasruck et al. | 378/53 |
| 2008/0137803 A1* | 6/2008 | Wu et al. | 378/5 |
| 2008/0253504 A1* | 10/2008 | Proksa | 378/5 |
| 2008/0253635 A1* | 10/2008 | Spies et al. | 382/131 |
| 2009/0016589 A1* | 1/2009 | Wolf et al. | 382/131 |
| 2010/0040192 A1* | 2/2010 | Zhang et al. | 378/8 |
| 2010/0135557 A1* | 6/2010 | Krauss et al. | 382/131 |

OTHER PUBLICATIONS

Clavijo et al., Image-quality optimization for dual energy computed tomography (DECT) three-material decomposition, Revista Ingenieria Biomedica, ISSN 1909-9762, vol. 3, No. 5, 2009, pp. 33-42.*

Granton et al., Implementation of dual- and triple-energy cone-beam micro-CT for postreconstruction material decomposition, Med Phys, 35 (11), Nov. 2008, pp. 5030-5042.*

Stolzmann et al., "Endoleaks after Endovascular Abdominal Aortic Aneurysm Repair: Detection with Dual-Energy Dual-Source CT," Radiology, vol. 249, No. 2, Nov. 2008, pp. 682-691.

Graser et al., "Dual-Energy CT in Patients Suspected of Having Renal Masses: Can Virtual Nonenhanced Images Replace True Nonenhanced Images?," Radiology, vol. 252, No. 2, Aug. 2009, pp. 433-440, radiology.rsnajnls.org.

* cited by examiner

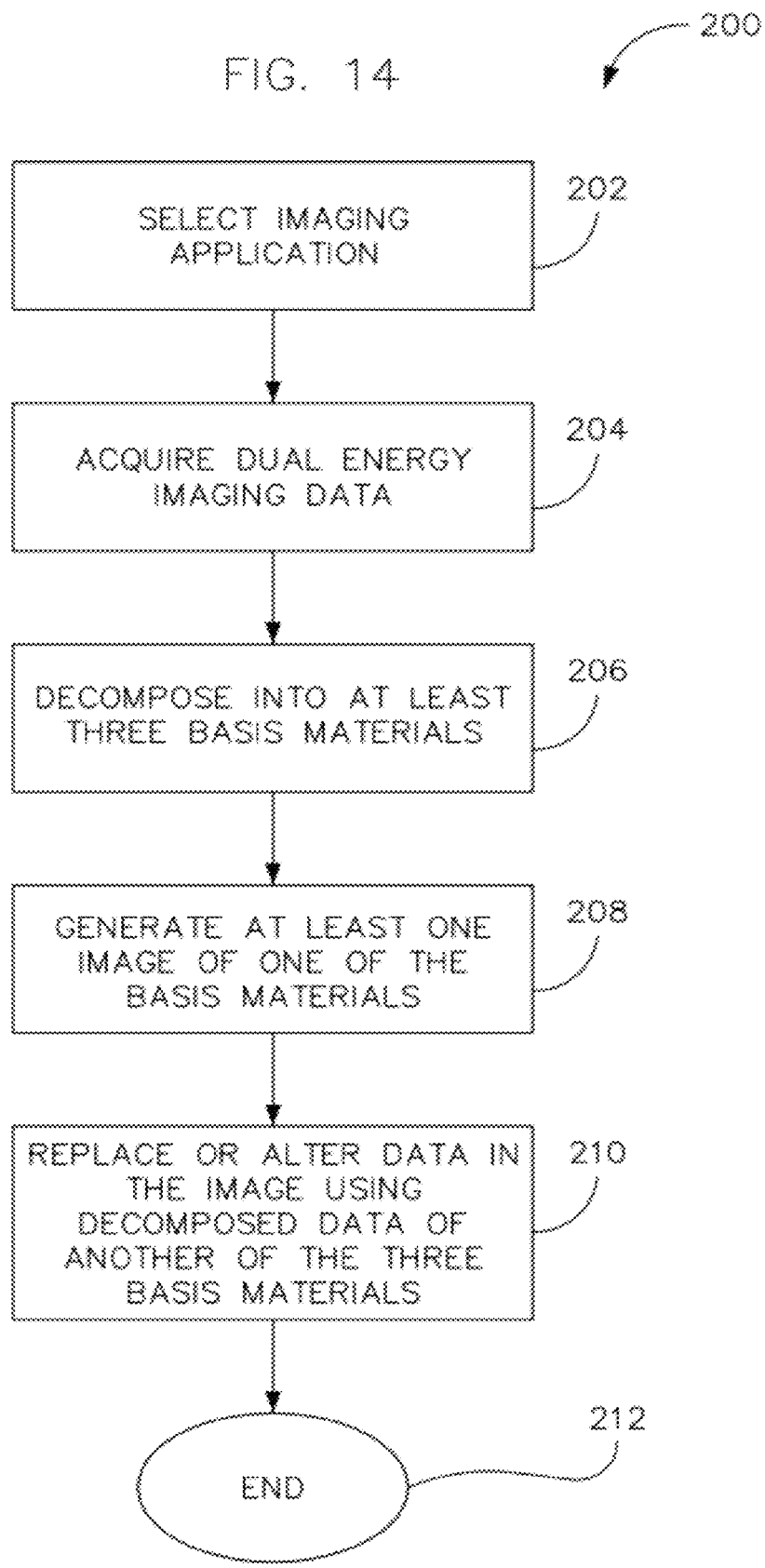

APPARATUS AND METHOD OF VISUALIZING MULTI-ENERGY IMAGING DATA

CROSS-REFERENCE TO RELATED APPLICATIONS

The present application is a continuation-in-part of and claims priority to U.S. patent application Ser. No. 12/315,184 filed Nov. 28, 2008, and also claims priority to U.S. Provisional Application 61/264,286 filed Nov. 25, 2009.

BACKGROUND

The subject matter disclosed herein relates to computed tomography (CT) imaging systems and, in particular, to a multi-material decomposition method and visualization method using dual energy x-ray sources for CT imaging systems.

Typically, in CT imaging systems, an x-ray source emits a fan-shaped or a cone-shaped x-ray beam toward a subject or object, such as a patient or a luggage item positioned on a support. The x-ray beam impinges on a detector assembly at the far side of the subject, comprising a plurality of detector modules, where the intensity of the x-ray beam detected is a function of the attenuation of the x-ray beam by the subject. In known "third generation" CT systems, the x-ray source and the detector assembly partially enclose the subject in a rotatable gantry structure. Data representing the intensity of the detected x-ray beam is collected across a range of gantry angles, and the data are ultimately processed to form an image.

A CT imaging system may be configured as an energy discriminating, a multi energy, and/or a dual energy CT imaging system. Dual energy CT imaging is an imaging procedure in which multiple scans are made of the same target under the same conditions at two different energy levels, or energy spectra, and is used to identify different materials in the target. For example, soft tissue and similar materials having a relatively low density typically attenuate incident x-rays to a lesser degree than does a relatively high density material, such as bone or an iodine contrast agent. It is appreciated in the relevant art that CT imaging performed at two imaging scans, one at a higher x-ray tube voltage level, such as 110 to 150 kVp, and another imaging scan performed at a lower x-ray tube voltage level, such as 60 to 80 kVp, provides more information about the materials being scanned than does a single-energy CT imaging scan.

Data obtained from a dual energy CT image scan can be used to reconstruct images using basis material decomposition computation processes. The generated images are representative of a pair of selected basis material densities. In addition to material density images, dual energy projection data can be used to produce a new image with x-ray attenuation coefficients equivalent to a selected monochromatic energy. Such a monochromatic image may include an image where the intensity values of image voxels are assigned as if a CT image were created by collecting projection data from the subject with a monochromatic x-ray beam.

In the medical imaging field, for example, dual energy CT scans may be performed at a relatively low energy' level of about 80 kVp, and at a relatively 'high energy' level of about 140 kVp, where the scans may be acquired "back-to-back" or interleaved. Special filters may be placed between the x-ray source and energy sensitive detectors such that different detector rows collect projections of different x-ray energy spectra.

The measurements may be obtained by: (i) scanning with two distinctive energy spectra; (ii) detecting photon energy according to energy deposition in the detector, and (iii) photon counting with multiple energy bins. In the absence of object scatter, the CT system can derive the information about object attenuation versus energy based on the signal from two or more regions of photon energy in the spectrum, for example, the low-energy and the high-energy portions of the incident x-ray spectrum. In medical CT, two physical processes dominate the x-ray attenuation: Compton scatter and the photoelectric effect. The detected signals from two energy regions usually provide sufficient information to resolve the energy dependence of the material being imaged. Furthermore, detected signals from the two energy regions provide sufficient information to determine the relative composition of an object composed of two materials.

Using the images obtained during these CT scans, one can generate basis material density images and monochromatic images, that is, images that represent the effect of performing a computed tomography scan with an ideal monochromatic tube source. Given a pair of material density images, it is possible to generate other basis material image pairs. For example, from a water and iodine image of the same anatomy, it is possible to generate a different pair of material density images such as calcium and gadolinium. Similarly, by using a pair of basis material images, one can generate a pair of monochromatic images, each at a specific x-ray energy. Similarly, one can obtain, from a pair of monochromatic images, a pair of basis material image pairs, or a pair of monochromatic images at different energies.

Conventional material basis decompositions utilize the concept that, in the energy region for medical CT, the x-ray attenuation of any given material can be represented by a proper density mix of two other materials, commonly denoted as "basis materials." The basis material decomposition computing process produces two CT images, each representing the equivalent density of one of the basis materials. Since a material density is independent of x-ray photon energy, the two CT images are largely free of beam-hardening artifacts. An operator can choose the basis material to target a certain material of interest, for example, to enhance the image contrast.

Thus, dual-energy CT is an imaging modality that extends the capabilities of standard CT, and enables the estimation of the full linear attenuation curve for each voxel in the image volume, instead of a scalar image in Hounsfield units. As explained above, this is achieved by acquiring X-ray projections at two different energy spectra and, under careful calibration, reconstructing a material-decomposed image pair. Each co-registered voxel of this pair is a two-dimensional vector corresponding to an estimate, consistent with projection data, for the density of two pre-selected materials making up that voxel. Because the space of linear attenuation curves can be described as a two-dimensional manifold plus a residual difference which is too small to be measured under current CT technology, this decomposition procedure is essentially limited to the specification of only two materials.

Typically, dual-energy CT provides estimates for a linear attenuation curve of an imaged object at each pixel location. However, a more desirable measurement would be a mass attenuation curve, which is the linear attenuation curve multiplied by a respective material density. Thus, the mass attenuation curve is density independent, and it shares with the linear attenuation curve the property that it can be represented as a weighted sum of the curves of other materials. However, the mass attenuation curve has an additional property that the weights in the sum have a defined physical meaning: that they are the mass fractions of the constituent materials in the mix. Therefore, their weights should add to "unity," or one.

As such, assuming that the mass fractions add to one, and that the mass attenuation coefficients relate back to the linear attenuation coefficients via their respective densities, an additional constraint is thereby imposed on a resulting system of equations that enables determination of at least a third material in a three material decomposition. Thus, triple material decomposition is possible if certain assumptions can be made regarding this additional constraint.

Solutions include an assumed relationship between given materials and the mixture by using a physicochemical model, as an example. One such solution includes assuming the mixture is an ideal solution, which implies that a volume of the solution at a given temperature and pressure is equal to the volume of its constituent parts at the same temperature and pressure. Under this assumption, the linear attenuation coefficients are thus assumed to be the volume fractions of the constituent materials in the mixture. As such, they add to one, providing an additional constraint over a two-material system and allowing a third material to be included in a decomposition that derives from two scans at different energies, resulting in three materials or a material triplet.

Thus, although an object to be imaged typically includes several materials, the object may be visualized having three top, or primary, materials selected for visualization. Once the three materials are determined as a material triplet, it is typically desirable to generate images of the three materials in order to diagnose a medical condition or to view images of materials of a security baggage scanner, as examples.

However, although a three material decomposition represents a dramatic improvement over a two material decomposition, which itself is a dramatic improvement over conventional single energy imaging, a three material combination is nevertheless a simplification that can cause confusion when viewing results. For instance, although an ability to view contrast agent as one of the materials of the material triplet may improve an ability to diagnose a pathology or condition, contrast agent displaces other materials within an image. Thus, it is possible that an image of a contrast agent as one of the materials of the material triplet may yield misleading results and blood flow, as an example, may be excluded and displaced by the contrast agent.

Additionally, a three material solution reveals three images as distinct and specific materials. However, as stated, a three material solution is itself a simplification, and some materials may not fall cleanly into one or another of the material triplet, despite the best material combination being selected to represent the overall set of materials being imaged.

Thus, there is a need for additional processing or manipulation of images in a three material system to better visualize an object being imaged.

BRIEF DESCRIPTION

The invention is directed to a system and method of visualizing multi-energy imaging data.

According to one aspect of the invention, an imaging system includes an x-ray source configured to emit a beam of x-rays toward an object to be imaged, a detector configured to receive x-rays that are attenuated by the object, a data acquisition system (DAS) operably coupled to the detector, and a computer operably coupled to the DAS and programmed to obtain scan data with two or more incident energy spectra, decompose the obtained scan data into at least three basis materials, generate an image of one of the at least three basis materials using the decomposed scan data, and replace at least one pixel in the image using decomposed data of another of the at least three basis materials.

According to another aspect of the invention, a method of multi-energy imaging includes selecting an imaging application for a multi-energy image acquisition, acquiring imaging data, based on the selected imaging application, with an x-ray source powered to a first keV and to a second keV, decomposing the acquired data into a three material combination, generating an image of a first material of the three material combination, and altering pixel data in the image using a imaging information of a second material of the three material combination.

According to yet another aspect of the invention, a computer readable storage medium having stored thereon a computer program configured to acquire energy-sensitive imaging data of an object, identify a material triplet of a multi-material combination, reconstruct an image based on the identified material triplets, and replace one material of the identified material triplet with another material of the identified material triplet in the image.

BRIEF DESCRIPTION OF THE DRAWINGS

FIG. 14 illustrates a technique for replacing or altering data of one image of a three material decomposition with pixel or material data from another image of the three material decomposition.

DETAILED DESCRIPTION

As noted above, conventional dual-energy CT scanner processing does not evaluate the composition of 'N≧3' materials in a material component mix, and is thus generally limited to a decomposition in only two materials (i.e., N=2). In an exemplary aspect of the disclosed method, the capabilities of the dual-energy CT scanner are expanded from producing a material-decomposed image pair to producing a material-decomposed image triplet. The image triplet is obtained by assuming that the various mixtures of substances and tissue types found in the human body have physicochemical properties substantially equivalent to those of what is herein denoted as an 'ideal material solution.' This can also be done by using a model for the excess free energy of the mixture. Using this equivalence provides a model for the density of an imaged material mixture, where the model complements the image information provided by the conventional CT data. Under this model, the mass attenuation curve of a particular voxel in a CT image is estimated, and a material-decomposed image triplet is derived (i.e., N=3). In another exemplary aspect of the disclosed method, more than three pre-selected materials can be decomposed by regularizing an otherwise under-constrained solution of a system of equations with a suitable function, and solving the resulting optimization problem. The disclosed method may also use pre-computed lookup tables for faster decomposition.

Figure 1:
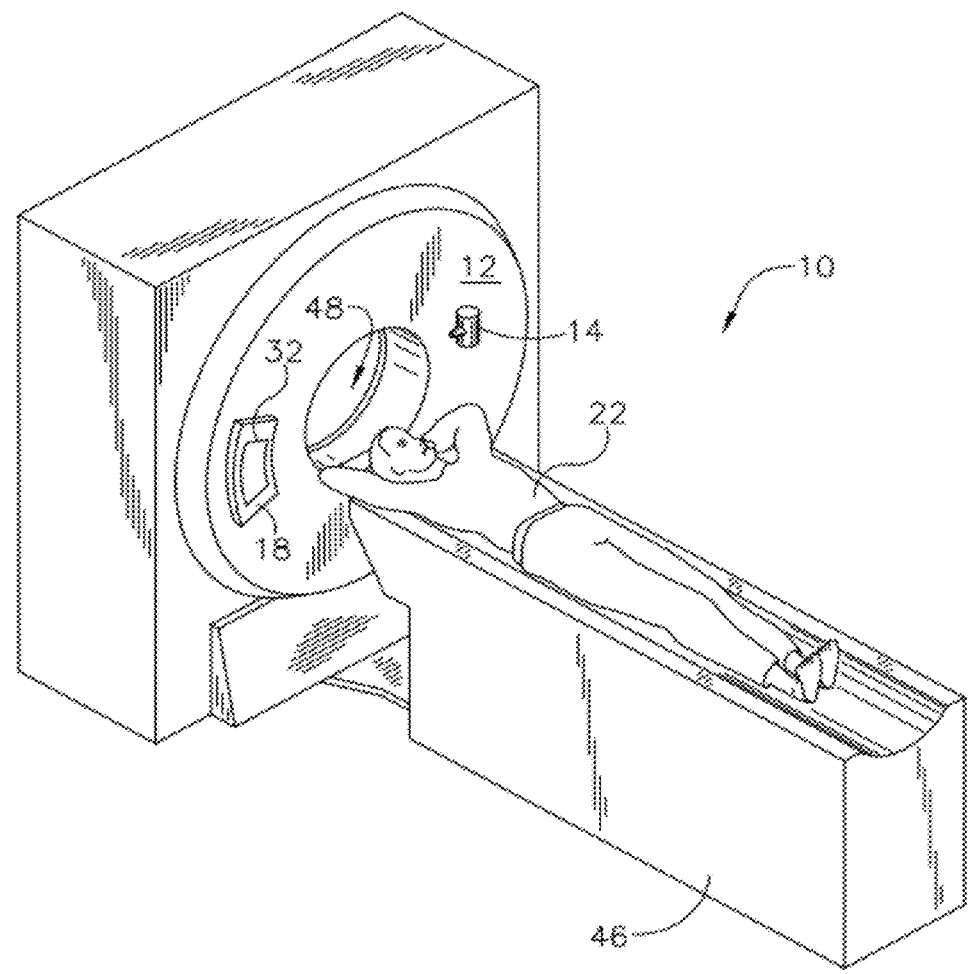
FIG. 1 is an isometric diagrammatical view of a CT imaging system, in accordance with the prior art.
Figure 2:
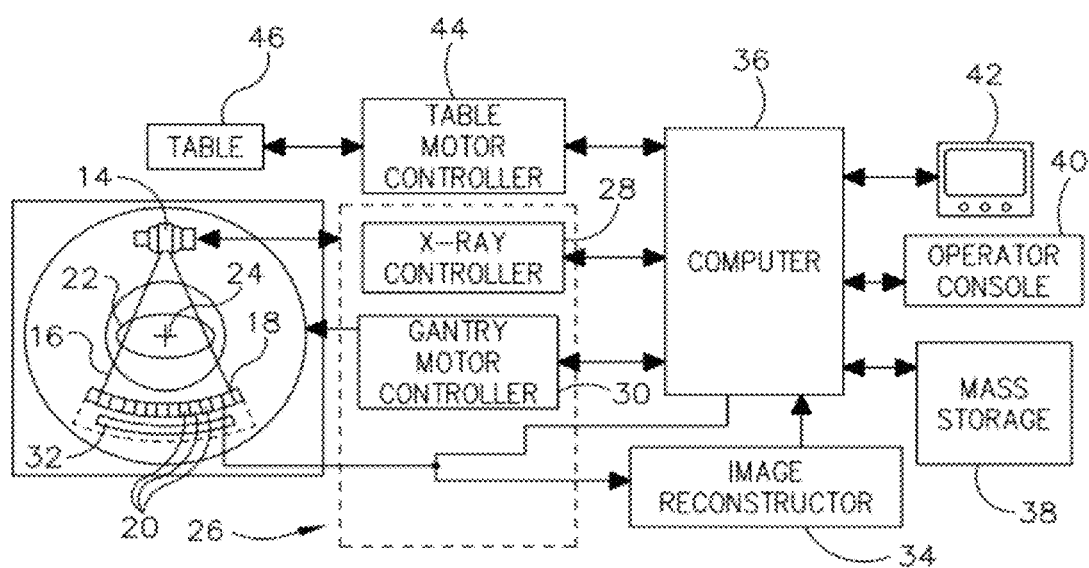
FIG. 2 is a functional block diagram of the CT imaging system of FIG. 1.

There is shown in the isometric diagrammatical illustration of FIG. 1 a dual-energy CT imaging system 10 configured to perform computed tomography imaging by means of photon counting and energy discrimination of x-rays at high flux rates, as is known in the relevant art. Imaging may be performed by, for example, a CT number difference decomposition, a basis material decomposition, a Compton and photoelectric decomposition, or a logarithmic subtraction decomposition. The dual-energy CT imaging system 10 comprises a gantry 12, with a collimator assembly 18, a data acquisition system 32, and an x-ray source 14 disposed on the gantry 12 as shown. A table 46 serves to move all or part of a patient 22 through a gantry opening 48 in the gantry 12.

The x-ray source 14 projects a beam of x-rays 16 through the patient 22 onto a plurality of detector modules 20 in a detector assembly which includes the collimator assembly 18 and the data acquisition system 32. In a typical embodiment, the detector assembly may comprise sixty four rows of voxel elements to enable sixty four simultaneous "slices of data" to be collected with each rotation of the gantry 12.

The plurality of detector modules 20 sense the projected x-rays that pass through the patient 22, and the data acquisition system 32 converts the data to digital signals for subsequent processing. Each detector module 20 produces an analog electrical signal that represents the intensity of an attenuated x-ray beam after it has passed through the patient 22. During a scan to acquire x-ray projection data, the gantry 12 rotates about a center of rotation 24 along with the x-ray source 14 and the detector assembly 15.

The rotation of the gantry 12 and the operation of the x-ray source 14 are controlled by a control mechanism 26. The control mechanism 26 includes an x-ray generator 28 that provides power and timing signals to the x-ray source 14, and a gantry motor controller 30 that controls the rotational speed and position of the gantry 12. An image reconstructor 34 receives sampled and digitized x-ray data from the data acquisition system 32 and performs high speed reconstruction. The reconstructed image is applied as an input to a computer 36 which stores the image in a mass storage device 38.

The computer 36 also receives commands and scanning parameters input from an operator console 40. An associated image display 42, such as a cathode ray tube, allows an operator to observe the reconstructed image and other data from the computer 36. The commands and scanning parameters are used by the computer 36 to provide control signals and information to the data acquisition system 32, the x-ray generator 28, and the gantry motor controller 30. In addition, the computer 36 operates a table motor controller 44 which controls the motorized table 46.

In conventional CT scanner processing, the data produced by the conventional system is an estimate of the linear attenuation curve of the imaged object at each voxel of the CT imaged volume of interest. A linear attenuation curve is a function that allows for the computation of the fraction of photons that travel undisturbed a fixed length of material at a certain density as a function of the energy of such photons. For example, the linear attenuation coefficient of liquid water is 0.294 $cm^{-1}$ for x-ray photon incident energy of 100 keV. That is, about 74.5% ($e^{-0.294}$) of the total number of incident photons with energy of 100 keV will be left undisturbed when traveling through 1.0 cm of liquid water having density of 1.00 $g/cm^3$. For photons with energy of 200 keV, the linear attenuation coefficient of liquid water is 0.243 $cm^{-1}$ and 78.4% ($e^{-0.243}$) of the total number of incident photons with energy of 200 keV will be left undisturbed when traveling though 1.0 cm of liquid water. In comparison, only 0.007% of photons with energy of 100 keV and 16.46% of photons with energy of 200 keV will travel undisturbed through 1.0 cm of iodine with a density of 4.93 $g/cm^3$ and a linear attenuation coefficient of 1.94 $cm^{-1}$.

The linear attenuation curve of substantially any material at substantially any density can be uniquely described as a weighted sum of the linear attenuation curves of two other materials. From a mathematical standpoint, the choice of materials (i.e., the material basis) is largely arbitrary but in practical applications the materials found in the imaged pairs are preferred. For example, in a clinical application the operator will generally select materials found in the human body, such as water, fat, and bone. Furthermore, for a given material basis and attenuation curve, the weighting coefficients may be uniquely defined such that the weighted sum of linear attenuation curves is equal to the original attenuation curve. Each weighting coefficient multiplying a linear attenuation curve of a given material can also be multiplied by the nominal density of the material, and the result is a material-density image pair, as shown in FIGS. 3-4.

Figure 3:
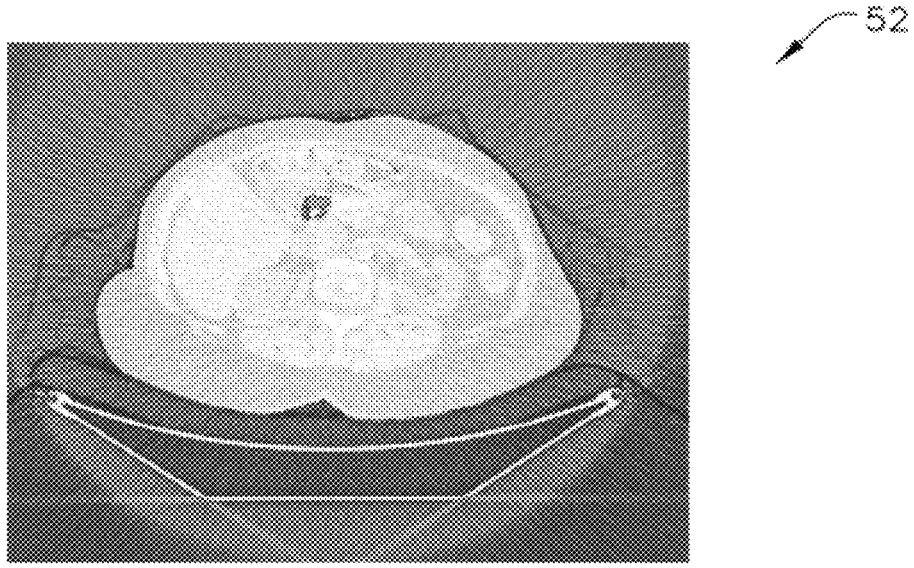
FIG. 3 is a water-component image from a decomposition in two materials, as may be provided by the CT imaging system of FIG. 1 operating in a dual energy mode.
Figure 4:
FIG. 4 is an iodine-component image from a decomposition in two materials, as may be provided by the CT imaging system of FIG. 1 operating in a dual energy mode.
Figure 5:
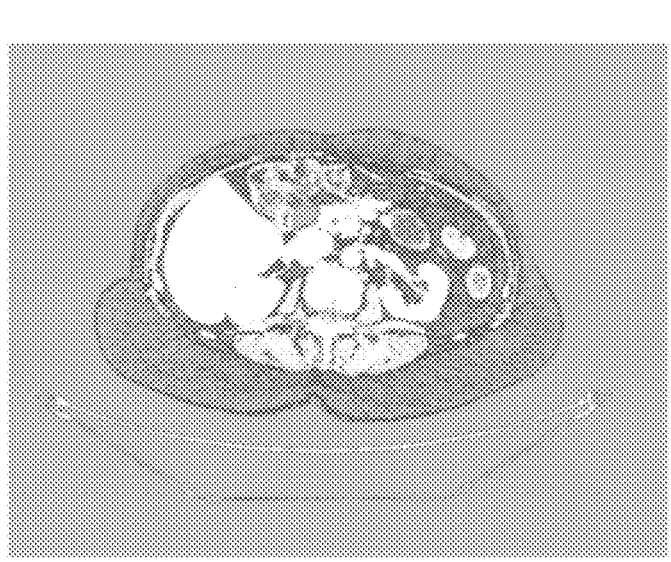
FIG. 5 is a monochromatic image showing attenuation at 70 keV, from a decomposition into two monochromatic images, as may be obtained by the CT imaging system of FIG. 1 operating in a dual energy mode.
Figure 6:
FIG. 6 is a monochromatic image showing attenuation at 140 keV, from a decomposition into two monochromatic images, as may be obtained by the CT imaging system of FIG. 1 operating in a dual energy mode.

Thus, the computer 36 may decompose a material-density image pair onto the image display 42, such as a water component image 52, shown in FIG. 3, and an iodine component image 54, shown in FIG. 4. In the iodine component image 54, the air region outside the body has resulted in an iodine-equivalent density comparable to that found inside the body. Alternatively, the computer 36 may decompose an energy image pair, such as a first monochromatic image 56 showing attenuation at 70 keV, shown in FIG. 5, and a second monochromatic image 58 showing attenuation at 140 keV, shown in FIG. 6. In the disclosed multi-material decomposition method, which can best be described with reference to a flow diagram 60 shown in FIG. 7, the dual-energy CT imaging system 10 acquires either a material-density image pair or an energy image pair from x-ray projections of two energy spectra, in step 62.

From a mathematical standpoint, there is no constraint on the values of the weighting coefficients necessary to represent a given linear attenuation cure through a weighted sum. Such weighting coefficients could, in principle, even be negative.

However, once a negative coefficient is multiplied by a nominal density to produce a density image, the user of the images is left with the problem of interpreting the meaning of the negative density values that result. It is also possible for the weight associated with the linear attenuation curve to assume a value greater than one, and producing a density value greater that the nominal density of the corresponding material. Accordingly, the capabilities of the dual-energy CT scanner 10 can be expanded from producing only a material-decomposed image pair to also producing a material-decomposed image pair more amenable to physical interpretation by enforcing the constraint that the weighting coefficients multiplying a linear attenuation curve must be non-negative and must be less than or equal to one.

In accordance with the disclosed method, the linear attenuation curve is divided by an actual (not nominal) material density to obtain a mass attenuation curve. The resulting mass attenuation curve is density independent, but is material dependent inasmuch as the mass attenuation curve can be represented as the weighted sum of the curves of other materials, similar to the linear attenuation curve. However, the mass attenuation curve has the additional attribute that the weighting coefficients have a well-defined physical meaning as mass fractions of the constituent materials in the material mix. As can be appreciated, the sum of the weighting coefficients in the mass attenuation curve is unity.

As explained in greater detail below, the weighting coefficients $\alpha$ in a weighted sum of linear attenuation coefficients can be related to the weighting coefficients $\beta$ in a weighted sum of mass attenuation coefficients through a model for how the materials in the material basis mix. For example, by assuming an ideal material solution, the constraint that the weighting coefficients $\beta$ sum to unity can also be imposed on the weighting coefficients $\alpha$. This allows for expressing the linear attenuation curve of a given material as a sum of three linear attenuation curves, instead of the conventional two curves. As understood in the relevant art, decomposition into two materials yields a unique pair of weighting coefficients, but without further constraints, the triplet material decomposition produces an infinite set of triplets of weighting coefficients. The set of triplets is one-dimensional, as each triplet in the set can be uniquely associated to a parameter. For any given choice of three materials, this parameter can be interpreted as a 'dial' that allows a user to select a triplet of weighting coefficients in the set. The corresponding triplet of weighting coefficients results in the same weighted sum of linear attenuation curves. The weighted sum is satisfied by an arbitrary choice of triplets in the set of triplets. However, if an external constraint is provided, only one 'dial setting' will yield a triplet that satisfies the constraint that the weighting coefficients $\alpha$ sum to unity. A relation between $\alpha$ and $\beta$ can be established if a model for the density of the mix of materials in a given material triplet is available.

In accordance with the disclosed method, physicochemical models can be used to establish relationships between the densities and quantities of given materials and the density of a mix of the given materials, so as to provide for triple material decomposition. One of the physicochemical models used may be that of an 'ideal solution.' The disclosed method works from the presumption that the mixture of component materials form an ideal solution, and thus that the volume of the ideal solution, at a given temperature and pressure, is equal to the volume of the component parts of the mix at the same temperature and pressure. Accordingly, it can be shown that the weighting coefficients $\alpha$ in the decomposition of a linear attenuation curve as the weighted sum of linear attenuation curves of other materials have a straightforward physical interpretation—that the weighting coefficients are the volume fractions of the component materials in the material mix.

Referring again to FIG. 7, a material basis is specified having (N≧3) material components, in step 64. The particular material components specified for the material basis may be selected from among the substances and tissue types identified as appearing in the material-density image pair or the energy image pair. In an exemplary embodiment, a selection of fat, bone, and blood may be made via the operator console 40.

It is known in the practice of dual-energy computed tomography that the linear attenuation coefficient of a given material is dependent on: (i) the energy E of the imaging x-rays, (ii) the mass density of the imaged materials, and (iii) the effective atomic number of the imaged materials. The linear attenuation coefficient $\mu_L(E)$ for a given material can be expressed as the sum $$\mu_L(E) = \sum_i^N \alpha_i \mu_{L,i}(E), \qquad (1)$$

where $\alpha_i$, i=1, 2, ... N are energy-independent constants and $\mu_{L,i}(E)$, i=1, 2, ... N are the linear attenuation curves of N arbitrarily pre-selected materials. For materials found in the human body and within the detection range of x-ray energies typically used in medical imaging, the linear attenuation coefficient $\mu_L(E)$ can be represented by a linear combination of component materials, commonly denoted as a 'material basis.' Thus, given a measurement of $\mu_L(E)$ at two distinct energy levels, for which $\mu_{L,1}$ and $\mu_{L,2}$ are known, unique solutions can be found for $\alpha_1$ and $\alpha_2$ so as to provide a material basis for two component materials. However, a conventional dual-energy CT scanner cannot decompose into a material basis having three or more component materials.

By introducing an additional constraint, the disclosed method provides for decomposition of a third component material. The relation in equation (1) can be expressed in terms of a 'mass attenuation coefficient' $\mu_M(E)$ that is related to the linear attenuation coefficient by the expression $$\mu_M(E) = \frac{\mu_L(E)}{\rho} \qquad (2)$$

where $\rho$ is the mass density of a given component material M, as the component material M is disposed within an imaged aggregate of component materials. Equation (1) can be rewritten as:

$$\mu_M(E) = \sum_i^N \beta_i \mu_{M,i}(E), \qquad (3)$$

where Equation (3) has the added constraints:

$$0 \leq \beta_i \leq 1; \text{ for } i = 1, 2, \ldots, N \qquad (4a)$$

$$\sum_i^N \beta_i = 1 \qquad (4b)$$

The coefficients $\beta_i$ are the mass fractions of each component material in the imaged aggregate of component materials. By establishing a relationship between the energy-independent coefficients $\alpha_i$ in Equation (1) and the mass fraction coefficients $\beta_i$ in Equation (2), an additional constraint is provided that provides for a further decomposition by the dual-energy CT scanner.

Figure 7:
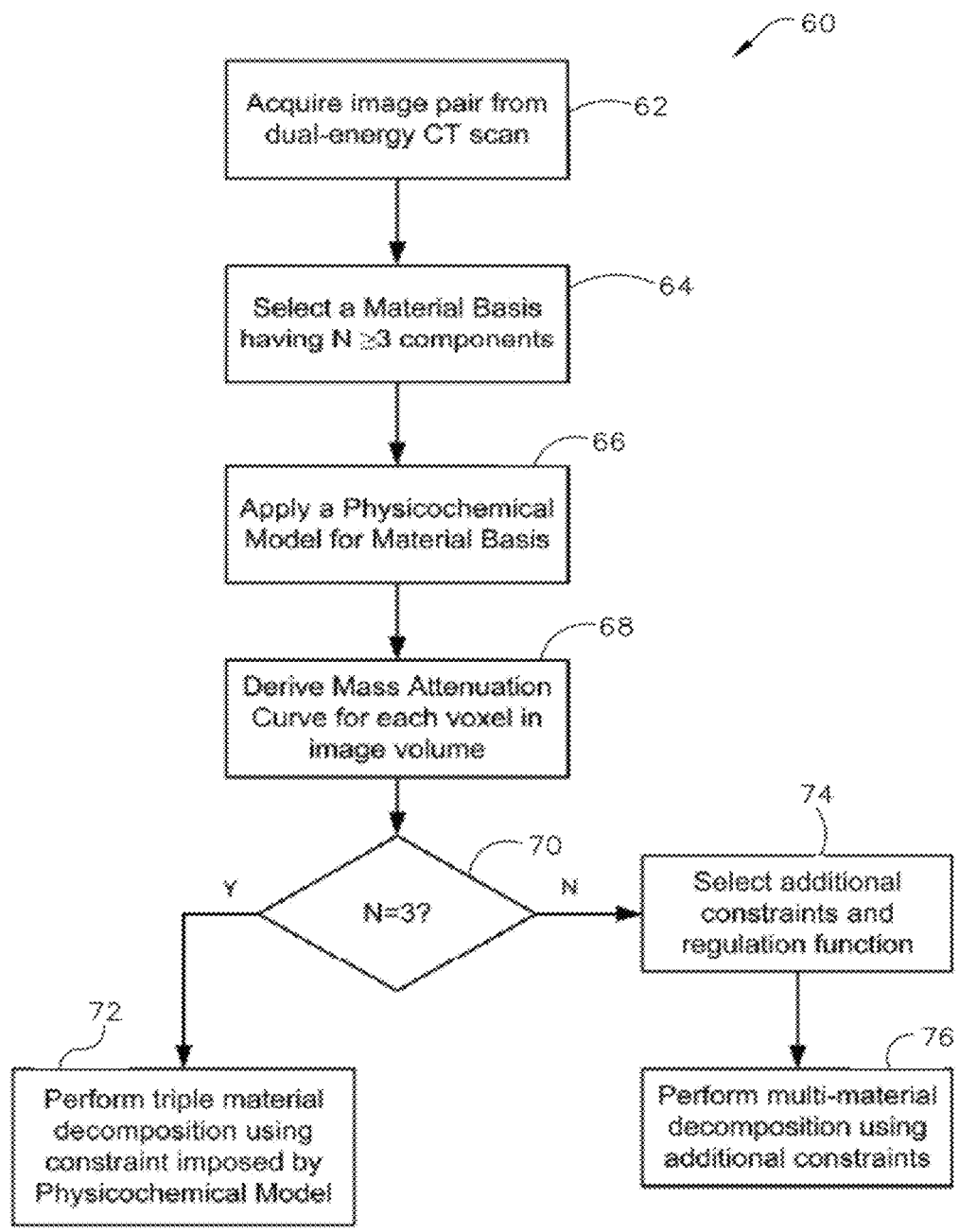
FIG. 7 is a flow diagram illustrating the operation of a dual-energy CT imaging system functioning to provide multi-material decomposition, in accordance with the disclosed method.

Referring again to the flow chart 60 of FIG. 7, a physicochemical model, or properties model, for relevant properties (density, volume, etc) of the selected material mix is applied, in step 66. The disclosed process uses a physicochemical model to determine the density of a material mix, bringing in one more constraint to the two constraints already available via the dual-energy image pair. This immediately allows for the decomposition of the images into a material triplet. One model for the density of the imaged aggregate of component materials can be derived by assuming that the component materials form an 'ideal solution,' that is, a component mixture having a volume at a given temperature and pressure essentially equal to the sum of the volumes of the individual component parts at the same temperature and pressure. It can be shown that this leads to the following constraints:

$$0 \leq \alpha_i \leq 1; \text{ for } i = 1, 2, \ldots, N \qquad (5a)$$

$$\sum_{i}^{N} \alpha_i = 1 \qquad (5b)$$

where $$\alpha_i = \frac{V_i}{\sum_{j=1}^{N} V_j} \qquad (6)$$

That is, a well-posed, triple-material decomposition can be obtained from a dual-energy CT scanner image pair by specifying that the component materials in the aggregate mixture of imaged materials comprise an ideal solution.

A derivation or estimate is made of the mass attenuation curve for each voxel in the image volume, at step 68. A determination is made, at decision block 70, whether three material basis components are being used (i.e., N=3). If the response is "yes," operation proceeds to step 72 at which the triple-material decomposition is solved. If, at decision block 70, the response is "no," a regularization function is selected, at step 74, to constrain the otherwise ill-posed solution of the multi-material decomposition problem. The multi-material decomposition is solved under the additional physicochemical constraints, at step 76, as described in greater detail below.

Figure 8:
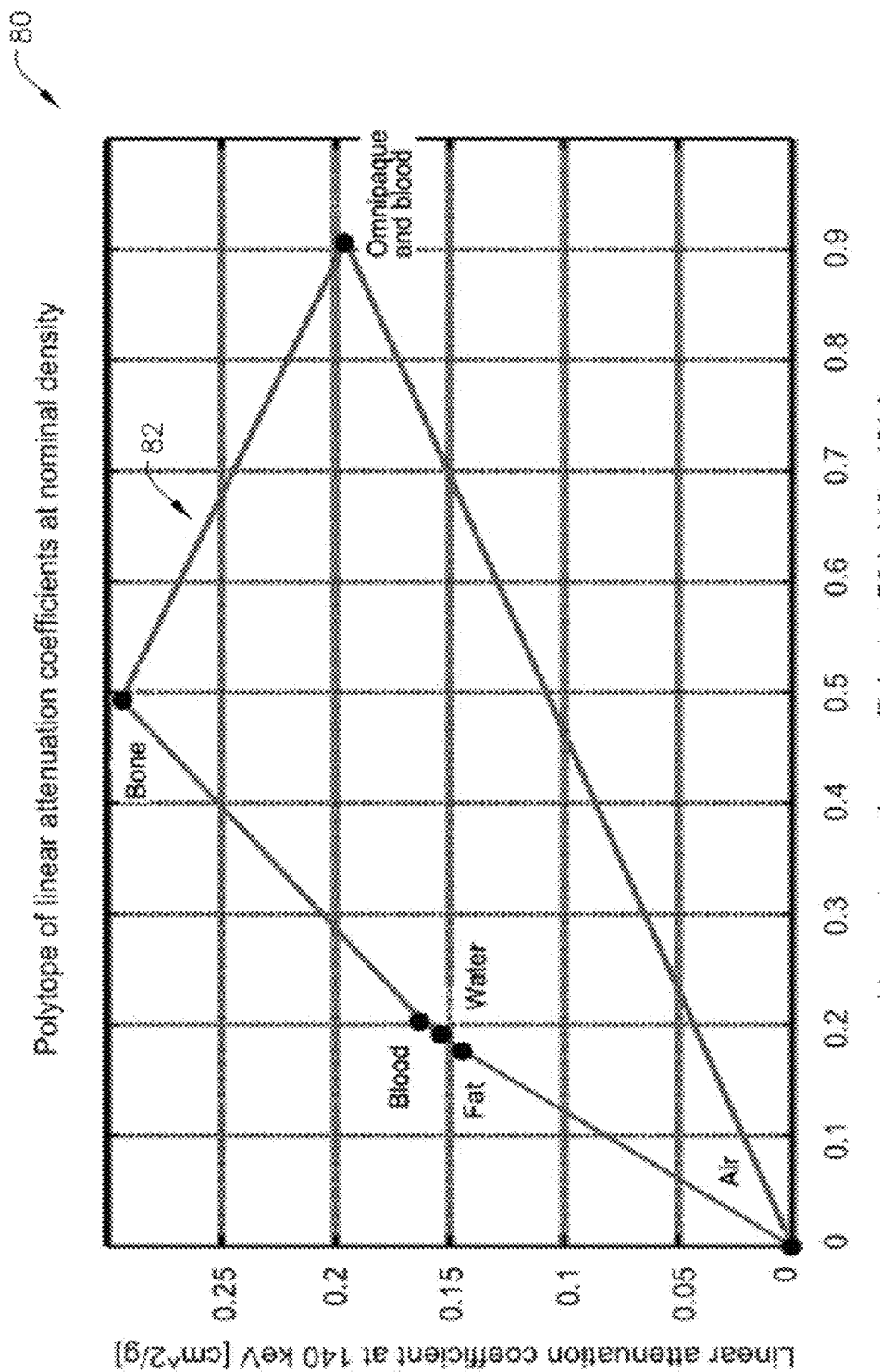
FIG. 8 is a graph illustrating a convex polytope of linear attenuation coefficients at nominal density.

By way of explanation for step 72, because of the constraints in equations (5a) and (5b), the energy-independent constants $\alpha_i$ in Equation (1) can be viewed as weights in a combination of the linear attenuation coefficients of the respective component materials, in the imaged aggregate of component materials, at the nominal material densities. It can be appreciated by one skilled in the art that material's linear attenuation properties at two arbitrary, but fixed, energy levels $E_1$ and $E_2$ can be represented as a point in a two-dimensional space having coordinates $\mu_L = (\mu_L)(E_1), \mu_L(E_2))E_1$. This may be exemplified by a graph 80, shown in FIG. 8. The graph 80 shows dual-energy linear attenuation coefficient values of N arbitrary materials plotted along orthogonal axes. When the material mix in the human body is modeled as an ideal solution, $\mu_L$ is inside the convex hull H of the set $\{\mu_{L,i}, i=1, 2, \ldots, N\}$. That is, the linear attenuation coefficients for a given energy pair fall within the convex hull 82 of the linear attenuation coefficients of the imaged aggregate of component materials.

However, for N>3, the condition that $\mu_L \in H$ serves to constrain only the range of the energy-independent coefficients $\alpha_i$, and is not adequate to fully specify the values of the coefficients $\alpha_i$. In this case, a unique solution can be obtained by adding the further constraint that a suitable function $f$ of the vector $\alpha = (\alpha_1, \alpha_2, \ldots, \alpha_N)$ is minimal, and an N-material decomposition for N>3 can be obtained by solving the optimization problem given by:

$$\alpha \ast = \min_{\alpha} f(\alpha) \qquad (7)$$

and by meeting the conditions of Equations 1, 5a, and 5b, above.

In accordance with the disclosed method, multi-material (N>3) decomposition is achieved through the introduction of further constraints on the weights of the weighted sum of the linear attenuation curves. Such further constraints include, for example, data-fidelity constraints, constraints based on the spatial dependency of voxels, and constraints derived from prior knowledge of the operator.

For N>3, the disclosed process can be further expanded by introducing a regularization function to the otherwise unconstrained solution of the N-material decomposition problem. The regularization function for determining the multiple material contributions, at step 76, can be selected depending on the anatomy that is being looked at based on a priori knowledge of the common characteristics of the material make-up of the relevant anatomy. For example, if the operator is looking at the liver, the regularization function may be tailored to favor water, iohexol, and blood over bone.

In an exemplary embodiment of the disclosed method, step 74 can be carried out off-line to create a lookup table for interactive visualization of the results. Multiple look up tables may be pre-generated with decompositions across different sets of materials. The particular table to be used for a decomposition can be chosen based on the anatomy/region of interest based on the a priori knowledge of the material make-up of that region. Moreover, the lookup tables may be generated 'on the fly' based on user input. The operator could specify the materials of interest based on some ambiguity to be resolved, or else interact with a scatter plot feature and to define the convex hull manually.

Figure 9:
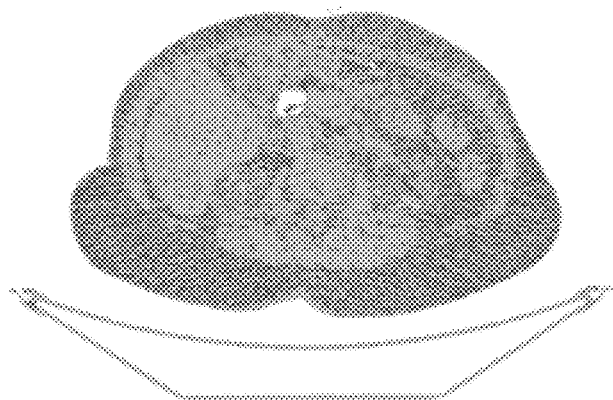
FIG. 9 is a an air-component image from a multi-material decomposition, obtained in accordance with the disclosed method.
Figure 10:
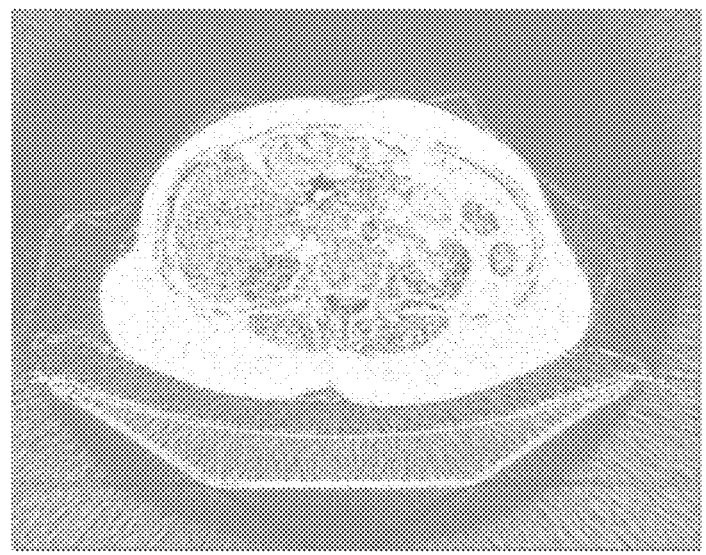
FIG. 10 is a fat-component image obtained from the multi-material decomposition process used to produce the image of FIG. 9.
Figure 11:
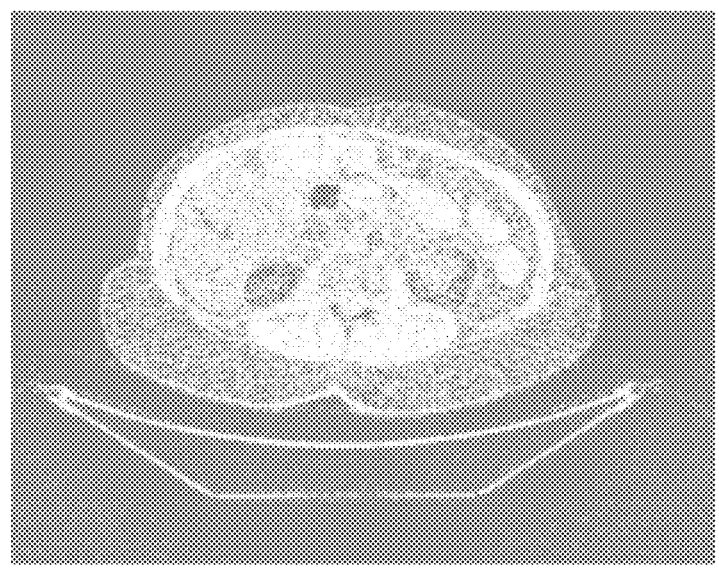
FIG. 11 is a blood-component image obtained from the multi-material decomposition process used to produce the image of FIG. 9.
Figure 12:
FIG. 12 is a bone-component image obtained from the multi-material decomposition process used to produce the image of FIG. 9.
Figure 13:
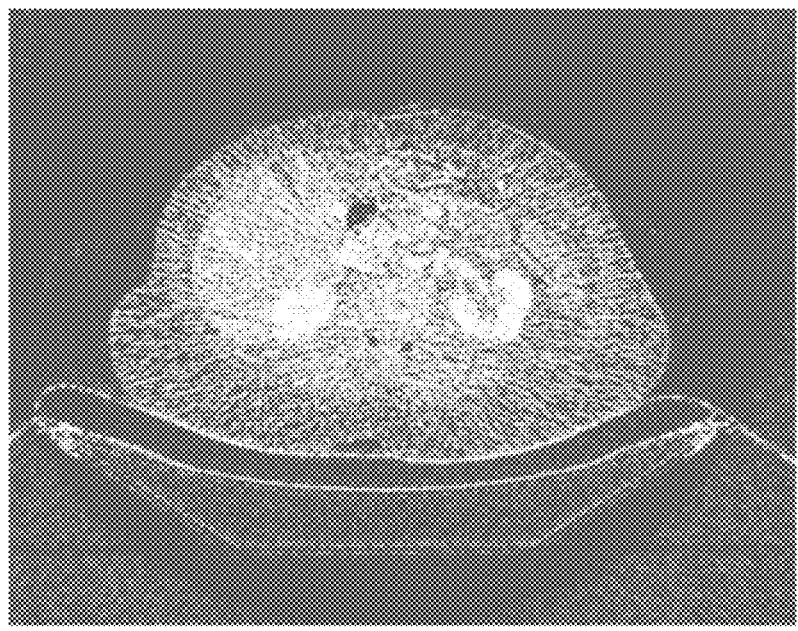
FIG. 13 is an Omnipaque-component image obtained from the multi-material decomposition process used to produce the image of FIG. 9.

Example of the multi-material decomposition performed at step 76 of flow chart 60 are provided in the images of FIGS. 9-13. FIG. 9 is an air component image obtained with multi-material decomposition. FIG. 10 is a fat component image, FIG. 11 is a blood component image, FIG. 12 is a bone component image, and FIG. 13 is an Omnipaque-component image. The images resulting from this type of multi-decomposition have fractional voxel values that represent the contribution from a particular material. These images can be leveraged in a number of ways, including without limitation, the following examples:

A weighting function on a monochromatic image to represent the attenuation due to a particular material—this would include the multiplication of a particular monochromatic image by the volume fraction image;

AIR image can be used to identify contours of the body and interior vacuous regions (e.g., used for lung segmentation by counting the number of crossings in and out of this AIR region);

Segmentation based on threshold volume fraction (e.g., bone is the region that is >90% volume fraction on the bone image);

Providing a color overlay on top of standard images showing color intensity based on volume fraction image;

Inputting to a generalized segmentation engine—where one or more volume fraction images that result from the multi-material decomposition procedure are used in a material segmentation process;

Generating a virtual non-contrast image by replacing volume fraction associated with a contrast agent such as Omnipaque with another component such as blood; and Liver fat quantification, or general fat quantification, by using a fat-volume fraction image.

The plurality of detector modules 20 sense the projected x-rays that pass through the patient 22, and the data acquisition system 32 converts the data to digital signals for subsequent processing. Each detector module 20 in a conventional system produces an analog electrical signal that represents the intensity of an attenuated x-ray beam after it has passed through the patient 22. During a scan to acquire x-ray projection data, the gantry 12 rotates about a center of rotation 24 along with the x-ray source 14 and the detector assembly 15.

Thus, as described, multi-material decomposition includes an algorithm that performs material decomposition over a number of different materials which, in one embodiment, may be a material triplet. This works in general, but can be made to work better if the three materials the algorithm must choose are defined based on the specific application at hand. Thus, a material triplet may be selected based on the anatomy that is being imaged. As stated and as an example, if an operator or imaging clinician is imaging a liver, then a material triplet may be based on water, iohexol, and blood.

For neuro applications, one set of materials may be more applicable than another set of materials for a kidney stone application, for example. Additionally, a virtual non-contrast application may include an additional set of materials. There may also be a workflow by which a set of materials may be defined for multi-material decomposition either from scratch or by starting from a reference starting point that is driven by the specific application.

Additional applications together with typical related materials of interest are listed below as examples:

1. Kidney stone characterization, and materials for different stones may include: cystine, struvite, uric acid, calcium oxalate;
2. Virtual non contrast: contrast agent, fat, water, blood, bone;
3. Soft plaque analysis and differentiation: fibrous, fatty, mixed plaque materials;
4. Body fat measurement based on water, bone;
5. Liver fat measurement based on water, iohexol, and blood;
6. Calcium-iodine separation for CT-angiography (CTA) exams based on calcium and iodine;
7. Calcium scoring for Cardiac exams (focus on calcium vs. noncalcium);
8. Qualitative perfusion measurements (looking at iodine fraction in tissue);
9. Gout (looking for uric acid deposits or crystallized uric acid).

Further, it is possible to select material options for a material triplet based on other aspects related to an imaging session and by using data that is typically available to an imaging clinician, or may be readily made available thereto. Such aspects include but are not limited to:

a) A preconfigured database identifying a list of materials as a set of point locations in the 2D scatter plot representation along with the nominal densities of such materials.

b) Mass attenuation curves of materials and their nominal densities.

c) Workflow where materials are suggested to the user or automatically selected based off scanned anatomy or application protocol.

d) Selecting a proper decomposition pair from a known volume fraction. For example, with contrast studies timing and blood flow are known, and an amount of omnipaque distributed is also known.

In some imaging applications, the presence of some materials may be known based on other aspects of the imaging application. For instance, a presence of contrast agent such as omnipaque may be known, based on knowledge that the imaging data acquired was obtained during a contrast injection. Then, for a given dataset, either a set of materials among which a decomposition is performed can be optimized, or more informed decisions about how a decomposition should be performed may be known or inferred. Material selection of a material triplet may be by a user or clinician who may then select the contrast agent as one of the materials of the material triplet, according to an embodiment of the invention.

Thus, presenting a list of three material combinations based on earlier obtained data, from the many thousands of total possible material combinations, can dramatically decrease time and effort for a user. For instance, by generating a reduced universe of possible material combinations and prompting a user or clinician to review the possible material combinations to select a combination, scanning resources can accordingly be reduced.

As such, the universe of possible material combinations may be downselected or reduced based on information that is known prior to obtaining imaging data. For instance, as stated, kidney stone characterization may be based on a content of cystine, struvite, uric acid, calcium oxalate. Thus, knowing a priori the possible materials associated with a kidney stone, the number of possible material triplet combinations may be vastly reduced, and a three material characterization may then be performed quickly and efficiently. Further, although the downselection process may not yield specifically only three materials for the clinician (i.e., kidney stone may be associated with four materials, cystine, struvite, uric acid, calcium oxalate), or known a priori information may include less than three materials (i.e., CTA exams based on calcium and iodine), the universe of possible material triplets may nevertheless be vastly reduced by making use of what information is known a priori, thus dramatically reducing time and resources to generate images and make a diagnosis based thereon.

Material triplet selection may be determined via user selection after prompting the user with a range of possible materials or material combinations. For instance, if one material is known or expected with a high degree of probability, based on a priori knowledge, then the user may be presented with a list of materials or material options that take into account the one known material, and a truncated or reduced list may then be generated. Thus, in this example, though the list of possible material triplets is not deterministically reduced to three options, the number of possible materials and material combinations is nevertheless dramatically reduced, according to the invention. Likewise, if for instance two materials are deemed to have a high degree of probability based on a priori information, such as water and bone, then the list of possible material triplets is dramatically reduced, yet more, when compared to the example having one known material.

Once a material triplet is identified, then images of one or more of the material triplets may be generated in order to diagnose a medical condition or pathology. However, in some instances a material may be displaced by another material, which can lead to misleading or inaccurate results. As such, referring to FIG. 14, a technique 200 includes a method of overlaying one material in an image with information from one or more other materials generated in a three material decomposition. Technique 200 includes selecting an imaging application at step 202. In embodiments of the invention, the imaging application includes but is not limited to a kidney stone characterization, a soft plaque analysis, a body fat measurement, a liver fat measurement, a CT-angiography, a calcium scoring cardiac exam, a perfusion measurement, and a gout assessment.

After selection of the imaging application at step 200, dual energy imaging data is acquired at step 204. The dual energy may be obtained having an x-ray source, such as x-ray source 14 of FIG. 1, energized to 80 keV and 140 keV, as examples. In alternate embodiments, the dual energy imaging data may be obtained in an imaging system having two more sources. After obtaining the dual energy imaging data at step 204, the imaging data is decomposed into at least three basis materials at step 206.

After decomposition, one or more images is generated of at least one of the basis materials at step 208. Once the one or more images is generated, then imaging data in at least one of the images may be replaced or altered, using decomposed data of another of the three basis materials, at step 210, according to embodiments of the invention. Technique ends at step 212.

Imaging information may be manipulated for visualization according to a number of techniques, according to the invention.
a) After performing multi-material decomposition volume fractions are obtained for each material for each voxel or pixel of data. These volume fractions can be applied as weights to CT data of any type—monochromatic, material density, effective-Z. This dampens or accentuates the material(s) of choice.
b) Another technique is to only show the monochromatic Hu attenuation due to materials of choice. That is, attenuation contributions can be selected for materials of interest. The similar concept can be applied to something like an effective Z—and the effective Z can be generated without a certain or specific material. In terms of workflow, a user has an ability to select k out of N materials to combine into a "virtual" monochromatic image.
c) Virtual Non-Contrast CT Images can be generated by decomposing into a set of materials that includes a contrast agent or a representation for the contrast agent. The fraction then associated with this contrast agent can be substituted with a representation for blood or water, as examples.

Volume fraction images may also be generated, according to embodiments of the invention. Such images include a simple display of volume fraction images. However, an image can also be displayed that contains a sum of k materials' volume fractions out of a total N materials, where k=N generates a unity image.

Images may be generated having color overlays therein, that can include a color overlay showing a "material map" for a given material or set of materials, as an example. This overlay can be configured to show different materials in different colors, or display a map that represents a sum of a subset of materials in the multi-material decomposition.

A MVFP (Maximum Volume Fraction Projection) image may be generated, according to an embodiment of the invention. In this embodiment, an MVFP can be applied to either a full volume, a thin slab, or a thick slab. Thus, a pixel value may be shown for a voxel that has a maximum volume fraction for a given material—for example, if iodine is a material of choice. Additionally, if an image mode is applied to a monochromatic image, a maximum Hu value would not be seen along a projection, but a Hu value which corresponds to a maximum volume fraction for iodine along the projection. As such, a vasculature may be shown, and not bone, compared to standard maximum intensity projection (MIP) imaging (since both bone and iodine have high Hu values, but only the iodine would have high iodine volume fraction).

The above-described methods can be embodied in the form of computer program code containing instructions embodied in one or more tangible media, such as floppy diskettes and other magnetic storage media, CD ROMs and other optical storage media, flash memory and other solid-state storage devices, hard drives, or any other computer-readable storage medium, wherein, when the computer program code is loaded into and executed by a computer, the computer becomes an apparatus for practicing the disclosed method.

A technical contribution for the disclosed method and apparatus is that is provides for a computer implemented to a multi-material decomposition method and visualization method using dual energy x-ray sources for CT imaging systems.

According to one embodiment of the invention, an imaging system includes an x-ray source configured to emit a beam of x-rays toward an object to be imaged, a detector configured to receive x-rays that are attenuated by the object, a data acquisition system (DAS) operably coupled to the detector, and a computer operably coupled to the DAS and programmed to obtain scan data with two or more incident energy spectra, decompose the obtained scan data into at least three basis materials, generate an image of one of the at least three basis materials using the decomposed scan data, and replace at least one pixel in the image using decomposed data of another of the at least three basis materials.

According to another embodiment of the invention, a method of multi-energy imaging includes selecting an imaging application for a multi-energy image acquisition, acquiring imaging data, based on the selected imaging application, with an x-ray source powered to a first keV and to a second keV, decomposing the acquired data into a three material combination, generating an image of a first material of the three material combination, and altering pixel data in the image using a imaging information of a second material of the three material combination.

According to yet another embodiment of the invention, a computer readable storage medium having stored thereon a computer program configured to acquire energy-sensitive imaging data of an object, identify a material triplet of a multi-material combination, reconstruct an image based on the identified material triplets, and replace one material of the identified material triplet with another material of the identified material triplet in the image.

While the invention is described with reference to exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system comprising:
   an x-ray source configured to emit a beam of x-rays toward an object to be imaged;
   a detector configured to receive x-rays that are attenuated by the object;
   a data acquisition system (DAS) operably coupled to the detector; and
   a computer operably coupled to the DAS and programmed to:
   obtain scan data with two or more incident energy spectra;
   present a list comprised of possible three material combinations of basis materials to a user based on an anatomy being imaged;
   prompt the user to select a material that is known or expected to be present based at least on the anatomy being imaged;
   truncate the list of possible three material combinations based on the user selection;
   prompt the user to select a material triplet from the truncated list of possible three material combinations;
   decompose the obtained scan data into the material triplet that is selected by the user, with a limitation that a component mixture comprises an ideal solution of all component materials, which comprises defining that a volume of the component mixture is equal to the sum of the volumes of each material of the selected basis material combination;
   generate an image using the decomposed scan data; and
   replace at least one pixel in the image using decomposed data of another of the material triplet.

2. The imaging system of claim 1 wherein the computer is programmed to generate the image by overlaying at least two materials in the image, and programmed to represent each of the at least two materials with different colors, wherein the replaced at least one pixel in the image is one of the at least two materials in the image that is overlayed.

3. The imaging system of claim 1 wherein the computer is programmed to replace the at least one pixel by replacing a pixel representing a contrast agent with a pixel representing one of water and blood.

4. The imaging system of claim 1 wherein the computer is programmed to calculate an effective Z at a pixel location based on at least two images that are generated from the material triplet, and replace the at least one pixel using the calculated effective Z at the pixel location.

5. The imaging system of claim 1 wherein the computer is programmed to prompt a user to select one material of the material triplet to be used to replace the at least one pixel in the image.

6. The imaging system of claim 1 wherein the computer is programmed to replace the at least one pixel with a sum of at least two pixels of the material triplet.

7. The imaging system of claim 1 wherein the list of possible three material combinations includes basis materials from a group of materials comprising cystine, struvite, uric acid, calcium oxalate, fat, water, blood, bone, plaque, fibrous material, iohexol, and iodine.

8. The imaging system of claim 1 wherein the computer is programmed to select an imaging application that is one of a kidney stone characterization, a soft plaque analysis, a body fat measurement, a liver fat measurement, a CT-angiography, a calcium scoring cardiac exam, a perfusion measurement, and a gout assessment.

9. The system of claim 1 wherein the computer is further programmed to define the ideal solution by defining the component mixture as equal to the sum of the volumes of each of three basis materials at the same temperature and pressure.

10. The system of claim 1 wherein the computer is further programmed to:
    establish a mathematical relationship between:
    1) weighting constants for linear attenuation coefficients of the material triplet, wherein the linear attenuation coefficients are derived in the decomposition of the acquired data; and
    2) mass fraction coefficients that weight the masses of component materials of the material triplet within the component mixture; and
    determine a mixture of the material triplet using the established mathematical relationship.

11. The method of claim 10 wherein the weighting constants for the linear attenuation coefficients are energy-independent constants.

12. The imaging system of claim 1 wherein:
    some of the list of possible three material combinations of basis materials include four possible component materials that are known a priori to be associated with the anatomy being imaged;
    some of the list of possible combinations of basis materials include less than the list of possible three material combinations that are known a priori to be associated with the anatomy being imaged; and
    the computer is programmed to generate the image using three basis materials.

13. A method of multi-energy imaging, the method comprising:
    selecting an imaging application for a multi-energy image acquisition;
    acquiring imaging data of an object, based on the selected imaging application, with an x-ray source powered to a first keV and to a second keV;
    generating a list comprised of possible three material combinations based on information that is known about the imaging application prior to acquiring the imaging data;
    prompting a user to select at least one material based on a priori knowledge of the object;
    reducing the list of possible three material combinations based on the selected at least one material;
    prompting the user to select a final three material combination from the reduced list of possible three material combinations;
    decomposing the acquired data into an aggregate mixture of the final three material combination by specifying that at least three component materials in the aggregate mixture of imaged materials comprise an ideal solution;
    generating an image of a first material of the final three material combination; and
    altering pixel data in the image using imaging information of a second material of the final three material combination.

14. The method of claim 13 wherein selecting the imaging application comprises selecting one of a kidney stone characterization, a soft plaque analysis, a body fat measurement, a liver fat measurement, a CT-angiography, a calcium scoring cardiac exam, a perfusion measurement, and a gout assessment.

15. The method of claim 13 wherein generating the image of the first material comprises generating the image by overlaying at least two materials in the image, and representing each of the at least two materials with different colors, wherein the replaced at least one pixel in the image is one of the at least two materials in the image that is overlayed.

16. The method of claim 13 comprising altering the pixel data by replacing a pixel representing a contrast agent with a pixel representing one of water and blood.

17. The method of claim 13 comprising calculating an effective Z at a pixel location based on at least two images that are generated from the decomposed data, and altering the pixel data using the calculated effective Z at the pixel location.

18. The method of claim 13 wherein decomposing the acquired data into the material combination comprises decomposing the material combination into materials that include one of cystine, struvite, uric acid, calcium oxalate, fat, water, blood, bone, plaque, fibrous material, iohexol, and iodine.

19. The method of claim 13 comprising specifying that component materials in the aggregate mixture of imaged materials comprise an ideal solution, and further specifying that the ideal solution is a component mixture having a volume at a given temperature and pressure essentially equal to a sum of the volumes of the final three material combination at the same temperature and pressure.

20. The method of claim 13 comprising:
establishing a mathematical relationship between:
1) weighting coefficients for linear attenuation of the three material combination, wherein the weighting coefficients are derived in the decomposition of the acquired data; and
2) mass fraction coefficients that weight mass amounts of the three material combination; and
decomposing the acquired data into the aggregate mixture using the established mathematical relationship.

21. The method of claim 20 wherein the weighting coefficients are energy-independent constants.

22. The method of claim 13 comprising:
generating the list of possible three material combinations using either four materials, or less than three materials, that are known to be associated with the imaging application prior to acquiring the imaging data; and
generating the image of the first material comprises generating the image of a three material combination.

23. A non-transitory computer readable storage medium having stored thereon a computer program configured to:
acquire energy-sensitive imaging data of an object;
identify a material triplet of a multi-material combination by being programmed to:
generate a list of possible material triplets that are known to be associated with an imaging application used to acquire the energy-sensitive imaging data of the object;
prompt a user to identify a material known or expected to be associated with the imaging data of the object;
truncate the list of possible material triplets based on the identified material;
present the truncated list to the user; and
prompt the user to select a material triplet from the truncated list;
generate a convex hull based on linear attenuation coefficient values of the material triplet;
model the selected material triplet as an ideal solution component mixture of all three materials of the selected material triplet and as a material mix whose composite attenuation coefficient falls within the convex hull;
reconstruct an image based on the selected material triplet; and
replace one material of the selected material triplet with another material of the selected material triplet in the image.

24. The computer readable storage medium of claim 23 wherein the replaced one material is an image contrast agent, and the another material is one of water and blood.

25. The computer readable storage medium of claim 23 wherein the computer is programmed to generate an image by being programmed to generate an image having multiple materials represented each as different colors, wherein the replaced material is represented by a first color that is overlayed with the another material that is the first color.

26. The computer readable storage medium of claim 23 wherein the list of possible material triplets comprises a combination of three materials selected from the group comprising cystine, struvite, uric acid, calcium oxalate, fat, water, blood, bone, plaque, fibrous material, iohexol, and iodine.

27. The computer readable storage medium of claim 23 wherein the computer program is configured to prompt the user to select an imaging application for imaging the object, wherein the imaging application comprises one of a kidney stone characterization, a soft plaque analysis, a body fat measurement, a liver fat measurement, a CT-angiography, a calcium scoring cardiac exam, a perfusion measurement, and a gout assessment.

28. The computer readable storage medium of claim 23 wherein the computer is programmed to model the selected material triplet as an ideal solution component mixture by being further programmed to specify the ideal solution component mixture as having a volume at a given temperature and pressure essentially equal to a sum of the volumes of individual component parts of the selected material triplet at the same temperature and pressure.

29. The computer readable storage medium of claim 23 wherein the computer is programmed to:
decompose the acquired energy-sensitive data into the selected material triplet;
establish a mathematical relationship between:
1) weighting constants for linear attenuation coefficients, wherein the linear attenuation coefficients are derived in the decomposition of the acquired energy-sensitive data; and
2) mass fraction coefficients that weight amounts of component materials of the selected material triplet; and
determine the selected material triplet using the established mathematical relationship.

30. The computer readable storage medium of claim 29 wherein the weighting constants for the linear attenuation coefficients are energy-independent constants.

31. The computer readable storage medium of claim 23 wherein the computer is programmed to:
generate the list of possible material triplets using either four materials, or less than three materials that are known to be associated with the imaging application, prior to acquiring the energy-sensitive imaging data.

* * * * *